United States Patent [19]

Schmidt

[11] Patent Number: 5,206,357

[45] Date of Patent: Apr. 27, 1993

[54] PROCESS FOR THE PREPARATION OF ALKYL GLYCOSIDES AND ALKYL POLYGLYCOSIDES

[75] Inventor: Stefan Schmidt, Recklinghausen, Fed. Rep. of Germany

[73] Assignee: Huels Aktiengesellschaft, Marl, Fed. Rep. of Germany

[21] Appl. No.: 783,247

[22] Filed: Oct. 28, 1991

[30] Foreign Application Priority Data

Jan. 17, 1991 [DE] Fed. Rep. of Germany ....... 4101252

[51] Int. Cl.$^5$ ................... C07H 15/00; C07H 17/00; C07G 3/00
[52] U.S. Cl. ................................... 536/18.6; 536/124
[58] Field of Search .................. 536/18.6, 124

[56] References Cited

U.S. PATENT DOCUMENTS 3,839,318 10/1974 Madsfield .......................... 536/18.6
4,923,976 5/1990 Arnaudis ............................ 536/18.6

FOREIGN PATENT DOCUMENTS 0077167 4/1983 European Pat. Off. .
0165721 12/1985 European Pat. Off. .

*Primary Examiner*—Ronald W. Griffin
*Attorney, Agent, or Firm*—Oblon, Spivak, McClelland, Maier & Neustadt

[57] ABSTRACT

Alkyl glycosides and alkyl polyglycosides are prepared by reacting saccharides and alcohols having 12 to 20 C atoms by acid catalysis in the presence of sodium hypophosphite and up to 1.3% by water, relative to the total of saccharides and alcohols, the molar ratio of saccharide to alcohol ranging from 1:5 to 1:10; and, after reaction is complete, neutralizing the reaction medium with an alkali metal hydroxide dissolved in an alcohol having 1 to 4 C atoms.

12 Claims, No Drawings

PROCESS FOR THE PREPARATION OF ALKYL GLYCOSIDES AND ALKYL POLYGLYCOSIDES

BACKGROUND OF THE INVENTION

1. Field of the Invention

The present invention relates to a one-step process for the preparation of alkyl glycosides and alkyl polyglycosides by acid-catalyzed reaction of saccharides with alcohols having 12 to 20 C atoms.

2. Description of the Background

Alkyl glycosides and alkyl polyglycosides having $C_{12}$- to $C_{20}$-alkyl radicals can be prepared completely or partially from renewable raw materials. These alkyl glycosides and alkyl polyglycosides are obtaining increasing importance because of their interesting surfactant properties and at the same time their very good biological degradability. For applications in the household and in the cosmetics field, these products must satisfy high aesthetic demands. There is therefore an interest in processes by which alkyl glycosides and alkyl polyglycosides can be prepared in transparent aqueous solutions of good color.

In order to prepare alkyl glycosides and alkyl polyglycosides having long-chain alkyl groups, it is possible initially to prepare alkyl glycosides and alkyl polyglycosides having $C_1$- to $C_6$-alkyl groups by glycosylation of saccharides with short-chain alcohols. These products are then converted into the desired alkyl glycosides and alkyl polyglycosides using long-chain alcohols by trans-glycosylation at elevated temperature. However, the products prepared in this way are dark-colored.

According to EP 0,165,721, the color of products of this type can be improved by multi-step bleaching with hydrogen peroxide and stabilized by the addition of compounds releasing sulfur dioxide. The brightening effect is only of short duration without sulfur dioxide.

EP 0,077,167 describes a one-step preparation process in which an aldose or a ketose is reacted directly with a long-chain alcohol in a molar ratio of 1:1.25 to 1:4. The reaction is carried out at low water contents in the presence of a reducing agent. The reducing agent used is chiefly hypophosphorous acid. The sodium hypophosphite likewise employed is used in amounts of less than 0.4%, relative to the saccharide. After the reaction, the product is neutralized with alkali, after which excess long-chain alcohol is removed by distillation. It has been found that this process leads to distinctly colored products when using alcohols having 12 to 20 C atoms and a need thereby exists for a method of decoloring alkyl glycosides and alkyl polyglycosides.

SUMMARY OF THE INVENTION

Accordingly, one object of the present invention is to improve the color of the products in the preparation of alkyl glycosides and alkyl polyglycosides.

Briefly, this object and other objects of the present invention as hereinafter will become more readily apparent can be attained in a method for the preparation of alkyl glycosides and alkyl polyglycosides by reacting saccharides and alcohols having 12 to 20 C atoms by acid catalysis in the presence of sodium hypophosphite and up to 1.3% by water, relative to the total of saccharides and alcohols, the molar ratio of saccharide to alcohol ranging from 1:5 to 1:10; and, after reaction is complete, neutralizing the reaction medium with an alkali metal hydroxide dissolved in an alcohol having 1 to 4 C atoms.

DETAILED DESCRIPTION OF THE PREFERRED EMBODIMENTS

Saccharide reactants employed in the reaction include aldoses and ketoses. Examples of these are glucose, mannose, galactose and fructose. Glucose is preferably used. Alcohols suitable for the present process include, for example, lauryl alcohol, myristyl alcohol, palmityl alcohol and stearyl alcohol. Mixtures of alcohols can also be employed. Alcohols having 12 to 16 C atoms are preferably used.

The saccharide/alcohol molar ratio is preferably in the range from 1:5 to 1:8.

Suitable catalysts include mineral acids and strong organic acids. Examples of these acids are sulfuric acid, phosphoric acid and p-toluenesulfonic acid. The catalyst is preferably employed in concentrations of 0.2 to 5%, relative to the saccharide.

The reaction is usually carried out at a temperature of 80° to 140° C. Temperatures of 90° to 120° C. are particularly preferred.

The reaction is carried out in the presence of 0.5 to 5% of sodium hypophosphite, relative to the saccharide employed. Amounts of 1 to 2% are preferred.

Care must be taken that the water content, which can be calculated before the reaction and determined during the reaction by Karl Fischer titration, does not exceed 1.3%, relative to the total saccharide and long-chain alcohol content. At higher water contents, the coloration of the products is distinctly darker.

Water formed during the reaction is immediately removed by distillation. The water content can thereby be kept at a low level. The water content is preferably in the range from 0.1 to 1%.

During the reaction, alkyl glycosides and alkyl polyglycosides are prepared. All products whose average degree of polymerization is greater than one are designated as alkyl polyglycosides. The average degree of polymerization is preferably in the range between 1 and 8.

The mixture is neutralized with an alcoholic alkali metal hydroxide solution. The short-chain alcohols used as solvents here are, for example, methanol, ethanol, isopropanol and butanol. Neutralization is preferably carried out using a 1 to 20% strength alcoholic alkali metal hydroxide solution. Methanolic potassium hydroxide is preferably used.

Pale-colored alkyl glycosides and alkyl polyglycosides are prepared by the process according to the invention. 50% strength aqueous solutions of these products in general have iodine color numbers of <10. Subsequent bleaching, for example with hydrogen peroxide, is not necessary. The products can be employed directly in the cosmetics and in the detergent fields without further treatment.

Having now generally described this invention, a further understanding can be obtained by reference to certain specific examples which are provided herein for purposes of illustration only and are not intended to be limiting unless otherwise specified.

EXAMPLE 1

225 g (1.25 mol) of anhydrous glucose, 1,215 g (6.25 mol) of a 75:25 mixture of n-dodecanol and n-tetradecanol, 3.6 g (0.035 mol) of concentrated sulfuric acid and 3.8 g (0.035 mol) of sodium hypophosphite are heated at 100° C. for 4 hours while stirring in a water-jet vacuum (20 hPa). After this time, glucose can no longer be detected in the reaction mixture. The water content at the start of the reaction: 0.30%

The reaction mixture is cooled to about 50° C. and adjusted to pH 6 to 7 using a 2% strength methanolic potassium hydroxide solution. Methanol and excess fatty alcohol are stripped off on a rotary evaporator. The solid residue is mixed with water in the ratio 1:1. The alkyl polyglycoside solution thus obtained is transparent and completely colorless.

Iodine color number: <2

EXAMPLE 2

225 g (1.25 mol) of anhydrous glucose, 1,215 g (6.25 mol) of a 75:25 mixture of n-dodecanol and n-tetradecanol, 4.6 g 0.045 mol) of concentrated sulfuric acid and 3.7 g (0.034 mol) of sodium hypophosphite are heated at 110° C. for 4 hours while stirring in a water-jet vacuum (20 hPa). After this time, glucose can no longer be detected in the reaction mixture. The water content at the start of the reaction: 0.30%. Work up of the reaction medium is carried out as in Example 1.

Iodine color number: 4 to 7

COMPARISON EXAMPLE A 45 g (0.25 mol) of anhydrous glucose, 121 g (0.625 mol) of a 75:25 mixture of n-dodecanol and n-tetradecanol, 175 mg (1.75 mmol) of concentrated sulfuric acid and 430 mg (3.25 mmol) of 50% strength hypophosphorous acid are heated at 100° C. for 6 hours while stirring in a water-jet vacuum (20 hPa). After this time, glucose can no longer be detected in the reaction mixture. However, black specks occur. The water content at the start of the reaction: 0.40%. Work up of the reaction medium is carried out as in Example 1. For neutralization, however, solid, pulverized sodium carbonate is used. An alkyl polyglucoside solution is obtained here which is interspersed with black specks.

COMPARISON EXAMPLE B 45 g (0.25 mol) of anhydrous glucose, 121 g (0.625 mol) of a 75:25 mixture of n-dodecanol and n-tetradecanol, 500 mg (5 mmol) of concentrated sulfuric acid and 185 mg (1.75 mmol) of sodium hypophosphite are heated at 100° C. while stirring in a water-jet vacuum (20 hPa). After a reaction time of 6 hours, glucose is still distinctly detectable in the mixture. The water content at the start of the reaction: 0.28%. Work up of the reaction medium is carried out as in Comparison Example A.

Iodine color number: 700 to 900

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A method for the preparation of alkyl glycosides and alkyl polyglycosides from which transparent aqueous solutions having good color can be prepared comprising: reacting saccharides and alcohols having 12 to 20 carbon atoms by acid catalysis in the presence of sodium hypophosphite and up to 1.3% by weight water, relative to the total of saccharides and alcohols, the molar ratio of saccharide to alcohol ranging from 1:5 to 1:10; and, after reaction is complete, neutralizing the reaction medium with an alkali metal hydroxide dissolved in an alcohol having 1 to 4 carbon atoms.

2. The process according to claim 1, wherein the saccharide/alcohol molar ratio ranges from 1:5 to 1:8.

3. The process according to claim 1, wherein the neutralization is carried out with a 1 to 20% strength alkali metal hydroxide solution.

4. The process according to claim 1, wherein the neutralization is carried out with a methanolic potassium hydroxide.

5. The process according to claim 1, wherein the saccharide is glucose.

6. The process according to claim 1, wherein said alcohol reactant has 12 to 16 carbon atoms.

7. The process according to claim 1, wherein the reaction is carried out in the presence of 0.1 to 1.0% of water.

8. The process according to claim 1, wherein the reaction is carried out at a temperature of 80° to 140° C.

9. The process according to claim 1, wherein the saccharide is glucose, mannose, galactose or fructose.

10. The process according to claim 1, wherein the alcohol is lauryl alcohol, myristyl alcohol, palmityl alcohol or stearyl alcohol.

11. The process according to claim 1, wherein the concentration of catalyst ranges from 0.2 to 5%, relative to the saccharide.

12. The process according to claim 1, wherein the amount of sodium hypophosphite ranges from 0.5 to 5%, relative to said saccharide.

* * * * *